US010828112B2

(12) United States Patent
Syverson et al.

(10) Patent No.: US 10,828,112 B2
(45) Date of Patent: Nov. 10, 2020

(54) METHODS AND SYSTEMS FOR SETTING TRAJECTORIES AND TARGET LOCATIONS FOR IMAGE GUIDED SURGERY

(71) Applicant: Mobius Imaging LLC, Shirley, MA (US)

(72) Inventors: Benjamin Syverson, Chicago, IL (US); Michael Harboun, Chicago, IL (US); Carlos Torres, Chicago, IL (US); David Vondle, Chicago, IL (US); Chris Gold, Chicago, IL (US); Todd Furlong, Goffstown, NH (US); Scott Coppen, Amesbury, MA (US); Anders Eriksson, Stockholm (SE)

(73) Assignee: Mobius Imaging LLC, Shirley, MA (US)

( * ) Notice: Subject to any disclaimer, the term of this patent is extended or adjusted under 35 U.S.C. 154(b) by 120 days.

(21) Appl. No.: 15/790,856

(22) Filed: Oct. 23, 2017

(65) Prior Publication Data

US 2018/0199999 A1 Jul. 19, 2018

Related U.S. Application Data

(60) Provisional application No. 62/411,055, filed on Oct. 21, 2016.

(51) Int. Cl.
*A61B 34/20* (2016.01)
*A61B 34/00* (2016.01)
(Continued)

(52) U.S. Cl.
CPC ........ *A61B 34/20* (2016.02); *A61B 17/00234* (2013.01); *A61B 34/00* (2016.02);
(Continued)

(58) Field of Classification Search
CPC ..... A61B 19/201; A61B 19/203; A61B 19/20; A61B 19/22; A61B 19/5244; A61B 19/50;
(Continued)

(56) References Cited

U.S. PATENT DOCUMENTS

| 5,799,055 | A | 8/1998 | Peshkin et al. |
| 5,921,992 | A | 7/1999 | Costales et al. |

(Continued)

FOREIGN PATENT DOCUMENTS

| CN | 201422918 Y | 3/2010 |
| CN | 201542641 U | 8/2010 |

(Continued)

OTHER PUBLICATIONS

International Search Report for Application No. PCT/US2017/057413 dated Feb. 21, 2018, 3 pages.
(Continued)

*Primary Examiner* — Vi X Nguyen
(74) *Attorney, Agent, or Firm* — Howard & Howard Attorneys PLLC

(57) ABSTRACT

A system for performing image-guided surgery includes an instrument having a first portion configured to define a trajectory into the body of a patient, a marker device and a user-interface component. A sensing device receives electromagnetic signals that are reflected or emitted from the marker device, and a processing system, coupled to the sensing device, includes at least one processor configured with processor-executable instructions to perform operations that include tracking the position and orientation of the instrument relative to the patient based on the signals received at the sensing device, receiving a signal from the user-interface component of the instrument indicating a user-input event, and saving the trajectory into the body of
(Continued)

the patient defined by the first portion of the instrument in response to receiving the signal.

13 Claims, 10 Drawing Sheets

(51) Int. Cl.
*A61B 34/30* (2016.01)
*A61B 17/00* (2006.01)
*A61B 90/00* (2016.01)
*A61B 34/10* (2016.01)

(52) U.S. Cl.
CPC .............. *A61B 34/30* (2016.02); *A61B 34/76* (2016.02); *A61B 90/00* (2016.02); *A61B 90/39* (2016.02); *A61B 2017/00119* (2013.01); *A61B 2017/00203* (2013.01); *A61B 2017/00212* (2013.01); *A61B 2017/00221* (2013.01); *A61B 2017/00734* (2013.01); *A61B 2034/107* (2016.02); *A61B 2034/2048* (2016.02); *A61B 2034/2055* (2016.02); *A61B 2034/2065* (2016.02); *A61B 2034/2068* (2016.02); *A61B 2034/2072* (2016.02); *A61B 2090/0818* (2016.02); *A61B 2090/372* (2016.02); *A61B 2090/373* (2016.02); *A61B 2090/376* (2016.02); *A61B 2090/3762* (2016.02); *A61B 2090/3945* (2016.02); *A61B 2090/3983* (2016.02)

(58) Field of Classification Search
CPC .............. A61B 19/00; A61B 17/00234; A61B 17/3403
See application file for complete search history.

(56) References Cited

U.S. PATENT DOCUMENTS

| | | | |
|---|---|---|---|
| 6,149,592 A | 11/2000 | Yanof et al. | |
| 6,236,875 B1 | 5/2001 | Bucholz et al. | |
| 6,275,725 B1 | 8/2001 | Cosman | |
| 6,533,455 B2 | 3/2003 | Graumann et al. | |
| 6,772,002 B2 | 8/2004 | Schmidt et al. | |
| 6,785,572 B2 | 8/2004 | Yanof et al. | |
| 7,194,120 B2 | 3/2007 | Wicker et al. | |
| 7,251,522 B2 | 7/2007 | Essenreiter et al. | |
| 7,587,235 B2 | 9/2009 | Wist et al. | |
| 7,699,877 B2 | 4/2010 | Davison | |
| 7,722,530 B2 | 5/2010 | Davison | |
| 7,799,036 B2 | 9/2010 | Davison et al. | |
| 8,016,835 B2 | 9/2011 | Birkmeyer et al. | |
| 8,046,054 B2 | 10/2011 | Kim et al. | |
| 8,118,488 B2 | 2/2012 | Gregerson | |
| 8,126,114 B2 | 2/2012 | Naylor et al. | |
| 8,394,144 B2 | 3/2013 | Zehavi et al. | |
| 8,454,583 B2 | 6/2013 | Perez-Cruet et al. | |
| 8,457,790 B2 | 6/2013 | Blondel et al. | |
| 8,509,503 B2 | 8/2013 | Nahum et al. | |
| 8,761,337 B2 | 6/2014 | Naylor et al. | |
| 8,795,188 B2 | 8/2014 | Maschke | |
| 8,974,460 B2 | 3/2015 | De la Fuente Klein et al. | |
| 9,008,757 B2 | 4/2015 | Wu | |
| 9,125,680 B2 | 9/2015 | Kostrzewski et al. | |
| 9,237,861 B2 | 1/2016 | Nahum et al. | |
| 9,259,282 B2 | 2/2016 | Azizian et al. | |
| 9,283,048 B2 | 3/2016 | Kostrzewski et al. | |
| 9,308,050 B2 | 4/2016 | Kostrzewski et al. | |
| 9,545,233 B2 | 1/2017 | Sirpad et al. | |
| 9,550,299 B2 | 1/2017 | Wolf et al. | |
| 9,833,292 B2 | 12/2017 | Kostrzewski et al. | |
| 10,004,562 B2 | 6/2018 | Kostrzewski et al. | |
| 10,039,476 B2 | 8/2018 | Nahum et al. | |
| 10,064,682 B2 | 9/2018 | Azizian et al. | |
| 10,076,385 B2 | 9/2018 | Shoham et al. | |
| 10,136,952 B2 | 11/2018 | Couture et al. | |
| 10,159,534 B2 | 12/2018 | Maillet et al. | |
| 2007/0156157 A1 | 7/2007 | Nahum et al. | |
| 2008/0183190 A1* | 7/2008 | Adcox ............... A61B 17/1655 606/130 |
| 2011/0137156 A1 | 6/2011 | Razzaque et al. | |
| 2012/0235883 A1* | 9/2012 | Border .................... G06F 1/163 345/8 |
| 2014/0003572 A1 | 1/2014 | Gregerson et al. | |
| 2014/0134586 A1* | 5/2014 | Stein .................... G09B 23/28 434/262 |
| 2014/0139215 A1 | 5/2014 | Gregerson et al. | |
| 2014/0249546 A1 | 9/2014 | Shvartsberg et al. | |
| 2014/0265182 A1 | 9/2014 | Stanton et al. | |
| 2014/0275953 A1 | 9/2014 | Gregerson et al. | |
| 2015/0016609 A1 | 1/2015 | Malinen et al. | |
| 2015/0202009 A1 | 7/2015 | Nussbaumer et al. | |
| 2015/0366624 A1 | 12/2015 | Kostrzewski et al. | |
| 2016/0030117 A1 | 2/2016 | Mewes | |
| 2016/0074123 A1 | 3/2016 | Bly et al. | |
| 2016/0081754 A1 | 3/2016 | Kostrzewski et al. | |
| 2016/0174914 A1 | 6/2016 | Lerch et al. | |
| 2016/0220320 A1 | 8/2016 | Crawford et al. | |
| 2016/0235492 A1 | 8/2016 | Morard et al. | |
| 2016/0278875 A1 | 9/2016 | Crawford et al. | |
| 2017/0071691 A1 | 3/2017 | Crawford et al. | |
| 2017/0079727 A1 | 3/2017 | Crawford et al. | |
| 2017/0172669 A1 | 6/2017 | Berkowitz et al. | |
| 2017/0231702 A1 | 8/2017 | Crawford et al. | |
| 2017/0239002 A1 | 8/2017 | Crawford et al. | |
| 2017/0239003 A1 | 8/2017 | Crawford et al. | |
| 2017/0239006 A1 | 8/2017 | Crawford et al. | |
| 2017/0245951 A1 | 8/2017 | Crawford et al. | |
| 2017/0252112 A1 | 9/2017 | Crawford et al. | |
| 2017/0258533 A1 | 9/2017 | Crawford et al. | |
| 2017/0258535 A1 | 9/2017 | Crawford et al. | |
| 2017/0312039 A1 | 11/2017 | Crawford et al. | |
| 2017/0348061 A1 | 12/2017 | Joshi et al. | |
| 2017/0360513 A1 | 12/2017 | Amiot et al. | |
| 2017/0360517 A1 | 12/2017 | Crawford et al. | |
| 2018/0000546 A1 | 1/2018 | Crawford et al. | |
| 2018/0110573 A1 | 4/2018 | Kostrzewski | |
| 2018/0116739 A1 | 5/2018 | Gogarty et al. | |
| 2018/0116740 A1 | 5/2018 | Gogarty et al. | |
| 2018/0125597 A1 | 5/2018 | Gogarty et al. | |
| 2018/0157238 A1 | 6/2018 | Gogarty et al. | |
| 2018/0185113 A1 | 7/2018 | Gregerson et al. | |
| 2018/0207794 A1 | 7/2018 | Sebring et al. | |
| 2018/0221098 A1 | 8/2018 | Forsyth et al. | |
| 2018/0235715 A1 | 8/2018 | Amiot et al. | |
| 2018/0250077 A1 | 9/2018 | Xu et al. | |
| 2018/0256259 A1 | 9/2018 | Crawford | |
| 2018/0271605 A1 | 9/2018 | Kostrzewski et al. | |
| 2018/0346008 A1 | 12/2018 | Nahum et al. | |
| 2019/0000561 A1 | 1/2019 | Decker et al. | |
| 2019/0000569 A1 | 1/2019 | Crawford et al. | |
| 2019/0021795 A1 | 1/2019 | Crawford et al. | |
| 2019/0021799 A1 | 1/2019 | Crawford et al. | |
| 2019/0021800 A1 | 1/2019 | Crawford et al. | |
| 2019/0029759 A1 | 1/2019 | McDonell | |
| 2019/0029765 A1 | 1/2019 | Crawford et al. | |
| 2019/0038362 A1 | 2/2019 | Nash et al. | |
| 2019/0053859 A1 | 2/2019 | Couture et al. | |
| 2019/0069961 A1 | 3/2019 | Smith et al. | |
| 2019/0099222 A1 | 4/2019 | Nahum et al. | |
| 2019/0117313 A1 | 4/2019 | Crawford | |
| 2019/0142533 A1 | 5/2019 | Itkowitz et al. | |
| 2019/0239964 A1 | 8/2019 | LeBoeuf, II et al. | |
| 2019/0269467 A1 | 9/2019 | Forsyth et al. | |
| 2019/0274765 A1 | 9/2019 | Crawford et al. | |

FOREIGN PATENT DOCUMENTS

| | | |
|---|---|---|
| CN | 101700184 B | 1/2011 |
| CN | 101579269 B | 4/2011 |
| CN | 101853333 B | 11/2012 |
| EP | 2356950 B1 | 8/2015 |
| WO | 2015115809 A1 | 8/2015 |

(56) References Cited

FOREIGN PATENT DOCUMENTS

| WO | 2016044934 A1 | 3/2016 |
| WO | 2016144875 A2 | 9/2016 |
| WO | 2017036340 A1 | 3/2017 |
| WO | 2017122202 A1 | 7/2017 |
| WO | 2018185729 A1 | 10/2018 |

OTHER PUBLICATIONS

English language abstract and machine-assisted English translation for CN 201422918 extracted from espacenet.com database on Jan. 9, 2020, 7 pages.

English language abstract and machine-assisted English translation for CN 201542641 extracted from espacenet.com database on Jan. 9, 2020, 10 pages.

English language abstract and machine-assisted English translation for CN 101700184 extracted from espacenet.com database on Jan. 9, 2020, 10 pages.

English language abstract and machine-assisted English translation for CN 101579269 extracted from espacenet.com database on Jan. 9, 2020, 8 pages.

English language abstract and machine-assisted English translation for CN 101853333 extracted from espacenet.com database on Jan. 9, 2020, 9 pages.

English language abstract and machine-assisted English translation for WO 2015/115809 extracted from espacenet.com database on Jan. 9, 2020, 8 pages.

English language abstract for WO 2017/036340 extracted from espacenet.com database on Jan. 9, 2020, 2 pages.

Pal jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.

Bluteau, J. et al., "Vibrotactile Guidance for Trajectory Following in Computer Aided Surgery", 2010 Annual International Conference of the IEEE Engineering in Medicine and Biology Society: Buoenos Aires, Argentina, Aug. 31-Sep. 4, 2010, pp. 2085-2088.

He, Changyu et al., "An Inertial and Optical Sensor Fusion Approach for Six Degree-of-Freedom Pose Estimation", Sensors, Vol, 15, No. 7, Jul. 8, 2015, pp. 16448-16465.

Howard, Thomas et al., "Improving Precision in Navigating Laparoscopic Surgery Instruments Toward a Planar Target Using Haptic and Visual Feedback", Frontiers in Robotics and AI, vol. 3, Jun. 24, 2016, 14 pages.

Machine-Assisted English Translation of pp. 46, 83 and 85 of Kruger, Timo, "Ein Moduiares Navigationssystem fur die Dentale Irnplantologie", Nov. 16, 2006, 3 pages, and original German language document, 144 pages.

\* cited by examiner

METHODS AND SYSTEMS FOR SETTING TRAJECTORIES AND TARGET LOCATIONS FOR IMAGE GUIDED SURGERY

RELATED APPLICATION

This application claims the benefit of priority to U.S. Provisional Application No. 62/411,055, filed on Oct. 21, 2016, the entire contents of which are incorporated by reference herein.

BACKGROUND

Computer-assisted surgical procedures, which may include image guided surgery and robotic surgery, have attracted increased interest in recent years. These procedures include the integration of a "virtual" three-dimensional dataset of the patient's anatomy, typically obtained using pre-operative or intra-operative medical imaging (e.g., x-ray computed tomography (CT) or magnetic resonance (MR) imaging), to the actual position of the patient and/or other objects (e.g., surgical instruments, robotic manipulator(s) or end effector(s) in the surgical area. These procedures may be used to aid the surgeon in planning a surgical procedure and may also provide the surgeon with relevant feedback during the course of surgical procedure. There is a continuing need to improve the safety and ease-of-use of computer-assisted surgical systems.

SUMMARY

Various embodiments include methods and systems for performing computer-assisted image-guided surgery, including robotically-assisted surgery.

Embodiments include a system for performing image-guided surgery that includes an instrument having a first portion configured to define a trajectory into the body of a patient, a marker device and a user-interface component, the system further including a sensing device configured to receive electromagnetic signals that are reflected or emitted from the marker device, and a processing system, coupled to the sensing device, having at least one processor configured with processor-executable instructions to perform operations that include tracking the position and orientation of the instrument relative to the patient based on the signals received at the sensing device, receiving a signal from the user-interface component of the instrument indicating a user-input event, and saving the trajectory into the body of the patient defined by the first portion of the instrument in response to receiving the signal.

Further embodiments include a method of performing image-guided surgery that includes tracking an instrument pose using a motion tracking system, determining a trajectory extending within a body of a patient based on the tracked instrument pose, tracking a motion of the instrument using the motion tracking system, and determining a target location within the body of the patient and along the trajectory based on the tracked motion of the instrument.

Further embodiments include an image guided surgery system that includes a motion tracking system for tracking motion of an instrument relative to the body of a patient, and a processing system, coupled to the motion tracking system, and having at least one processor configured with processor-executable instructions to perform operations including determining a trajectory extending within the body of a patient based on a pose of the instrument, tracking a motion of the instrument using the motion tracking system, and determining a target location within the body of the patient and along the trajectory based on the tracked motion of the instrument.

Further embodiments include a method for performing image guided surgery that includes tracking a surgical instrument using optically-based motion tracking, tracking the surgical instrument using inertial navigation when the optically-based motion tracking is not available, and notifying a user when an accuracy criteria for the inertial navigation is not satisfied.

Further embodiments include a system for performing image-guided surgery that includes a surgical instrument having at least one inertial sensor and an optical marker device fixed thereto and a transmitter for transmitting data from the surgical instrument, a sensing device configured to receive electromagnetic signals that are reflected or emitted from the optical marker device, a receiver for receiving data transmitted from the surgical instrument, and a processing system, coupled to the sensing device and to the receiver, and including at least one processor configured with processor-executable instructions to perform operations including tracking a surgical instrument using optically-based motion tracking, tracking the surgical instrument using inertial navigation when the optically-based motion tracking is not available, and notifying a user when an accuracy criteria for the inertial navigation is not satisfied.

Further embodiments include a marker device including a rigid frame having a plurality of optical markers disposed on the frame, an inertial measurement unit mounted to the marker device, a power source, electronic circuitry coupled to the power source and to the inertial measurement unit, the electronic circuitry including a wireless transmitter for transmitting measurement data from the inertial measurement unit to an external device, and a rigid attachment member attached to the rigid frame at a first end and having a second end that is attached to at least one of a surgical instrument, a portion of a patient's anatomy and a robotic arm.

Further embodiments include a method for performing image guided surgery that includes identifying one or more features within the body of a patient in an image dataset of the patient's anatomy, registering the image dataset including the identified one or more anatomical features within a patient coordinate system, tracking a surgical instrument within the patient coordinate system, and actuating a haptic feedback mechanism on the surgical instrument based on the tracked position and/or orientation of the instrument with respect to the identified feature within the body of the patient.

Further embodiments include a system for performing image-guided surgery including a surgical instrument having a haptic feedback mechanism, a motion tracking system for tracking the surgical instrument within a patient coordinate system, a processing system, coupled to the surgical instrument and to the motion tracking system, and including at least one processor configured with processor-executable instructions to perform operations including identifying one or more features within the body of a patient in an image dataset of the patient's anatomy, registering an image dataset of the internal anatomy of a patient within the patient coordinate system, and actuating the haptic feedback mechanism based on the tracked position and/or orientation of the instrument with respect to the identified feature within the body of the patient.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
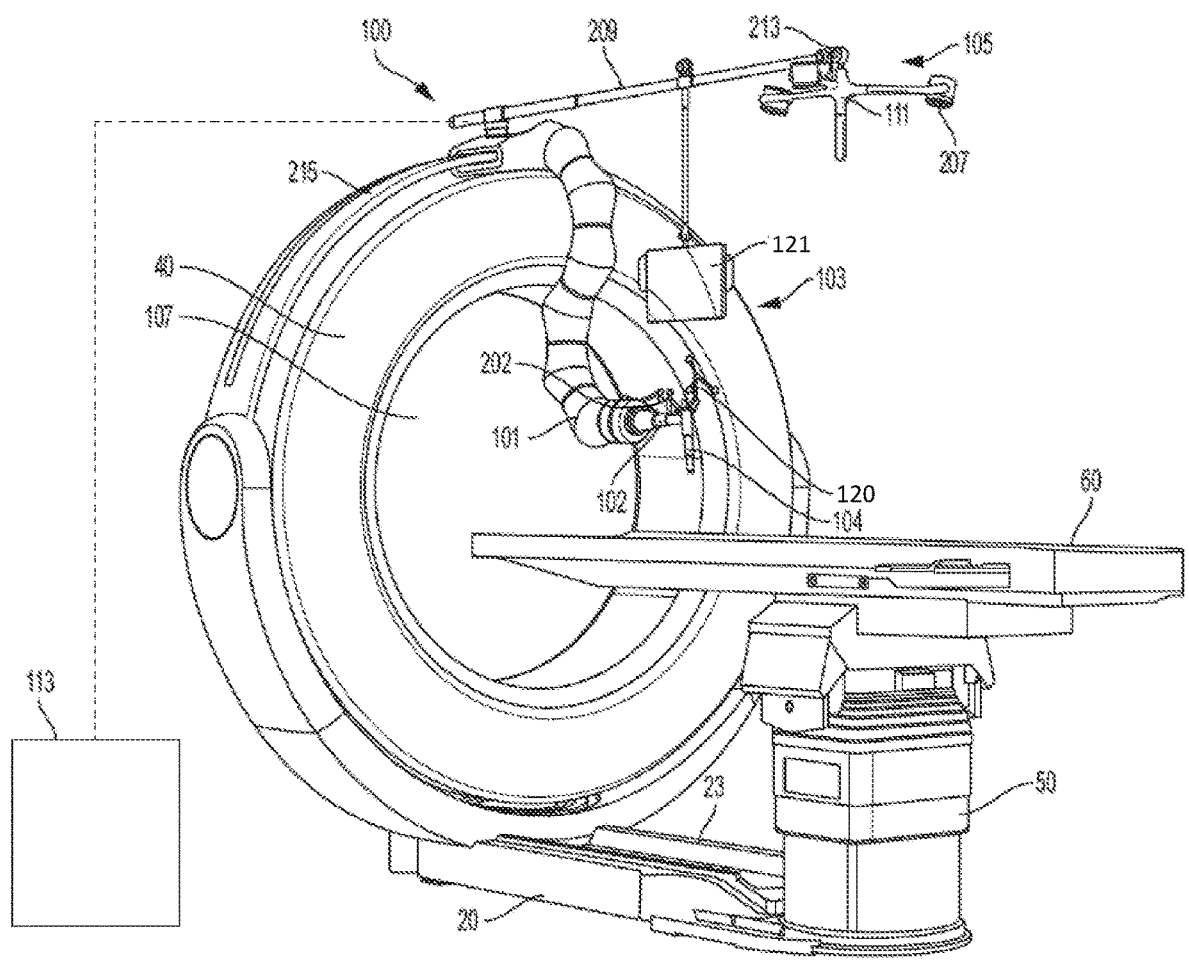
FIG. 1 is a perspective view of a system for performing robotically-assisted image-guided surgery according to an embodiment.

FIG. 1 illustrates a system 100 for performing computer-assisted image-guided surgery according to various embodiments. The system 100 in this embodiment includes an imaging device 103, a motion tracking system 105 and a robotic arm 101 for performing a robotically-assisted surgical procedure. The robotic arm 101 may comprise a multi joint arm that includes a plurality of linkages connected by joints having actuator(s) and optional encoder(s) to enable the linkages to rotate, bend and/or translate relative to one another in response to controlaaerg signals from a robot control system. The robotic arm 101 may be fixed to a support structure at one end and may have an end effector 102 at the other end of the robotic arm 101.

The imaging device 103 may be used to obtain diagnostic images of a patient (not shown in FIG. 1), which may be a human or animal patient. In embodiments, the imaging device 103 may be an x-ray computed tomography (CT) imaging device. The patient may be positioned within a central bore 107 of the imaging device 103 and an x-ray source and detector may be rotated around the bore 107 to obtain x-ray image data (e.g., raw x-ray projection data) of the patient. The collected image data may be processed using a suitable processor (e.g., computer) to perform a three-dimensional reconstruction of the object. In other embodiments, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure), intra-operatively (i.e., during a surgical procedure) or post-operatively (i.e., following a surgical procedure) by positioning the patient within the bore 107 of the imaging device 103. In the system 100 of FIG. 1, this may be accomplished by moving the imaging device 103 over the patient to perform a scan while the patient may remain stationary.

Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182 and U.S. Patent Application Publication No. 2014/0275953, the entire contents of all of which are incorporated herein by reference. In the embodiment shown in FIG. 1, the patient support 60 (e.g., surgical table) upon which the patient may be located is secured to the imaging device 103, such as via a column 50 which is mounted to a base 20 of the imaging device 103. A portion of the imaging device 103 (e.g., an O-shaped imaging gantry 40) which includes at least one imaging component may translate along the length of the base 20 on rails 23 to perform an imaging scan of the patient, and may translate away from the patient to an out-of-the-way position for performing a surgical procedure on the patient.

An example imaging device 103 that may be used in various embodiments is the AIRO® intra-operative CT system manufactured by Mobius Imaging, LLC and distributed by Brainlab, AG. Other imaging devices may also be utilized. For example, the imaging device 103 may be a mobile CT device that is not attached to the patient support 60 and may be wheeled or otherwise moved over the patient and the support 60 to perform a scan. Examples of mobile CT devices include the BodyTom® CT scanner from Samsung Electronics Co., Ltd. and the O-Arm® surgical imaging system form Medtronic, plc. The imaging device 103 may also be a C-arm x-ray fluoroscopy device. In other embodiments, the imaging device 103 may be a fixed-bore imaging device, and the patient may be moved into the bore of the device, either on a surgical support 60 as shown in FIG. 1, or on a separate patient table that is configured to slide in and out of the bore. Further, although the imaging device 103 shown in FIG. 1 is located close to the patient within the surgical theater, the imaging device 103 may be located remote from the surgical theater, such as in another room or building (e.g., in a hospital radiology department).

The motion tracking system 105 shown in FIG. 1 includes a plurality of marker devices 120, 202 and an optical sensor device 111. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

Figure 2A:
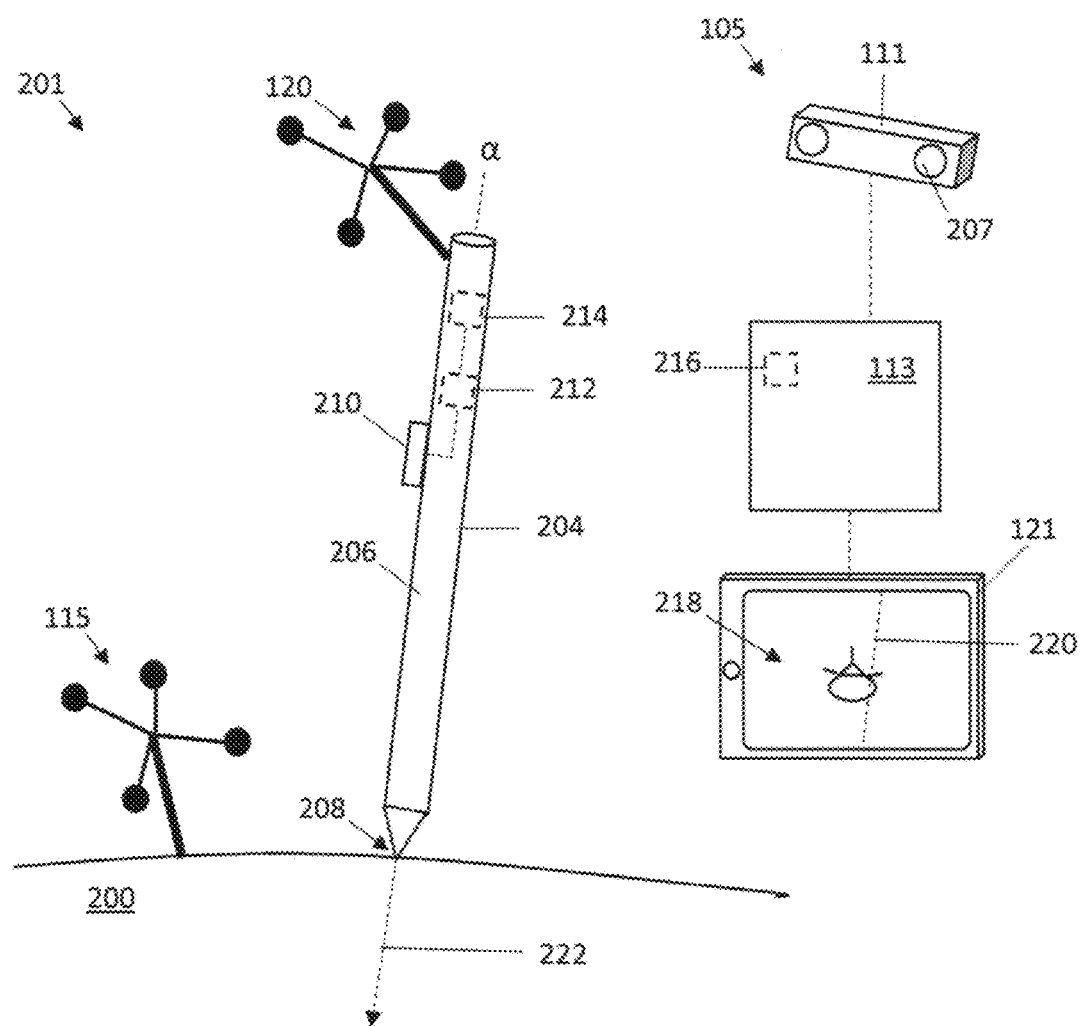
FIGS. 2A-2C schematically illustrate a gesture-based method for setting a trajectory and target location within a patient using a tracked instrument.
Figure 2B:
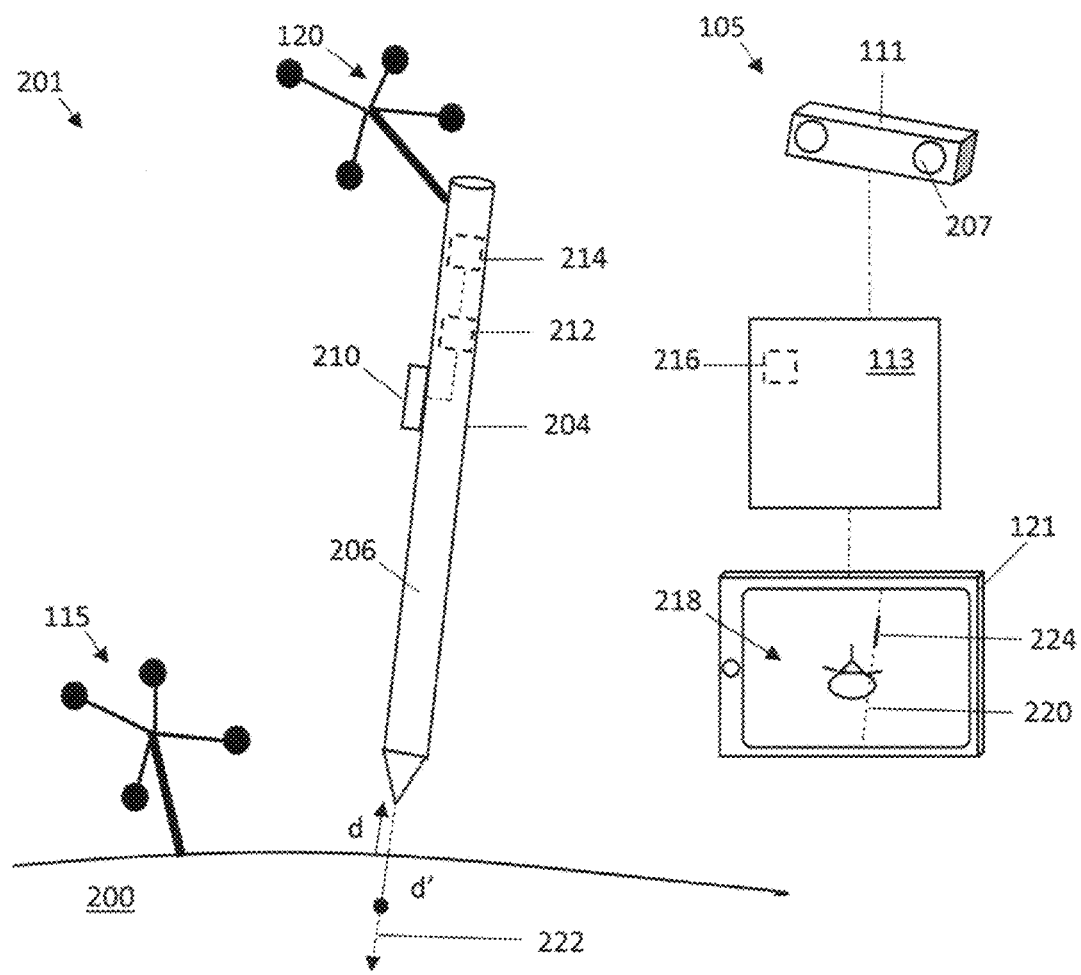
Figure 2C:
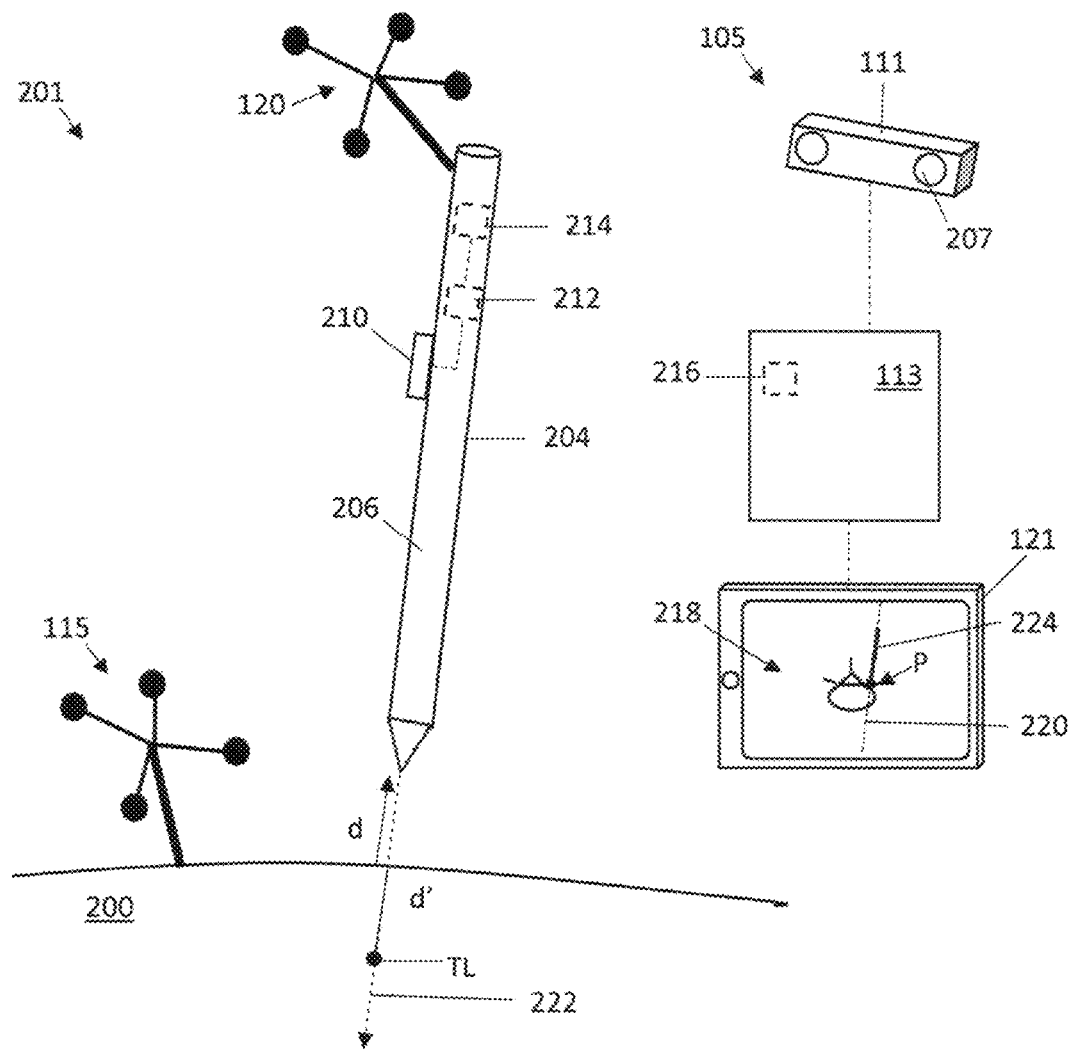

The motion tracking system 105 in the embodiment of FIG. 1 includes a plurality of marker devices 120, 202 and a stereoscopic optical sensor device 111 that includes two or more cameras 207 (e.g., IR cameras). The optical sensor device 111 may include one or more radiation sources (e.g., diode ring(s)) that direct radiation (e.g., IR radiation) into the surgical field, where the radiation may be reflected by the marker devices 120, 202 and received by the cameras. The marker devices 120, 202 may each include three or more (e.g., four) reflecting spheres, which the motion tracking system 105 may use to construct a coordinate system for each of the marker devices 120, 202. A computer 113 may be coupled to the sensor device 111 and may determine the transformations between each of the marker devices 120, 202 and the cameras using, for example, triangulation techniques. A 3D model of the surgical space in a common coordinate system may be generated and continually updated using motion tracking software implemented by the computer 113. In embodiments, the computer 113 may also receive image data from the imaging device 103 and may register the image data to the common coordinate system as the motion tracking system 105 using image registration techniques as are known in the art. In embodiments, at least one reference marker device 115 may be attached to the patient 200, as shown in FIGS. 2A-2C. The reference marker device 115 may be rigidly attached to a landmark in the anatomical region of interest (e.g., clamped or otherwise attached to a bony portion of the patient's anatomy) to enable the anatomical region of interest to be continually tracked by the motion tracking system 105. Additional marker devices 120 may be attached to surgical tools or instruments 104 to enable the tools/instruments 104 to be tracked within the common coordinate system. Another marker device 202 may be rigidly attached to the robotic arm 101, such as on the end effector 102 of the robotic arm 101, to enable the position of robotic arm 101 and end effector 102 to be tracked using the motion tracking system 105. The computer 113 may also include software configured to perform a transform between the joint coordinates of the robotic arm 101 and the common coordinate system of the motion tracking system 105, which may enable the position and orientation of the end effector 102 of the robotic arm 101 to be controlled with respect to the patient 200.

In addition to passive marker devices described above, the motion tracking system 105 may alternately utilize active marker devices that may include radiation emitters (e.g., LEDs) that may emit radiation that is detected by an optical sensor device 111. Each active marker device or sets of active marker devices attached to a particular object may emit radiation in a pre-determined pulse pattern (e.g., with modulated pulse width, pulse rate, time slot and/or amplitude) and/or wavelength which may enable different objects to be uniquely identified and tracked by the motion tracking system 105. One or more active marker devices may be fixed relative to the patient, such as secured to the patient's skin via an adhesive membrane or mask, or secured to bony anatomy via a clamp or other attachment mechanism. Additional active marker devices may be fixed to surgical tools 104 and/or to the end effector 102 of the robotic arm 101 to allow these objects to be tracked relative to the patient.

In further embodiments, the marker devices may be passive maker devices that include moiré patterns that may enable their position and orientation to be tracked in three-dimensional space using a single camera using Moiré Phase Tracking (MPT) technology. Each moiré pattern marker may also include a unique identifier or code that may enable different objects within the camera's field of view to be uniquely identified and tracked. An example of an MPT-based tracking system is available from Metria Innovation Inc. of Milwaukee, Wis. Other tracking technologies, such as computer vision systems and/or magnetic-based tracking systems, may also be utilized.

As shown in FIG. 1, the optical sensor device 111 may include a plurality of cameras 207 attached to a rigid support 235 mounted to an arm 209 extending above the patient surgical area. The optical sensor device 111 may include at least two cameras 207, and in embodiments three or more (e.g., four) cameras 207 attached to a rigid support 235. The arm 209 may be mounted to or above the imaging device 103. The arm 209 may enable the sensor device 111 to pivot with respect to the arm 209 and/or the imaging device 103 (e.g., via one or more ball joints 213). The arm 209 may enable a user to adjust the position and/or orientation of the sensor device 111 to provide the cameras 207 with a clear view into the surgical field while avoiding obstructions. The arm 209 may enable the position and/or orientation of the sensor device 111 to be adjusted and then locked in place during an imaging scan or surgical procedure.

The system 100 may also include at least one display device 121 as illustrated in FIG. 1. The display device 121 may display image data of the patient's anatomy obtained by the imaging device 103. In the case of CT image data, for example, the display device 121 may display a three-dimensional volume rendering of a portion of the patient's anatomy and/or may display two-dimensional slices (e.g., axial, sagittal and/or coronal slices) through the 3D CT reconstruction dataset. The display device 121 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 105 may be shown on the display 121, and may be shown overlaying the image data. The use of tracked surgical instruments or tools in combination with pre-operative or intra-operative images of the patient's anatomy in order to guide a surgical procedure may be referred to as "image-guided surgery."

In embodiments, the display device 121 may be a handheld computing device. As used herein, "handheld computing device" and "handheld display device" are used interchangeably to refer to any one or all of tablet computers, smartphones, pendant controllers, cellular telephones, personal digital assistants (PDA's), netbooks, e-readers, laptop computers, palm-top computers, wearable computers, and similar portable electronic devices which include a programmable processor and memory coupled to a display screen and may include hardware and/or software to enable display of information, including patient information and/or images, on the display screen. A handheld computing device typically also includes an antenna coupled to circuitry (e.g., a transceiver) to enable wireless communication over a network. A handheld computing or display device may be characterized by a sufficiently compact and lightweight structure to enable a user to easily grasp, maneuver and operate the device using one or both hands.

One or more handheld display devices 121 may be mounted to an arm 209 extending above the patient surgical area, as shown in FIG. 1. The arm 209 may also support the optical sensing device 111 for the motion tracking system 105, as described above. The one or more display devices 121 may be suspended from the arm 209, and the position of a display device 121 may be adjustable along the length of the arm 209. The display device 121 may be located within a sterile case or holder, such as described in U.S. application Ser. No. 15/701,063, filed on Sep. 11, 2017, which is incorporated by reference herein. In other embodiments, a handheld display device 121 may be mounted to the patient support 60 or column 50 or to any portion of the imaging system 103, or to any of the wall, ceiling or floor in the operating room, or to a separate cart. Alternately or in addition, the at least one display device 121 may be a monitor display that may be located on a mobile cart or mounted to another structure (e.g., a wall) within the surgical theater.

As shown in FIG. 1, the robotic arm 101 may be fixed to the imaging device 103, such as on a support element 215 (e.g., a curved rail) that may extend concentrically over the outer surface of the O-shaped gantry 40 of the imaging device 103. In embodiments, an arm 209 to which the optical sensing device 111 is mounted may be mounted to the same or a similar support element 215 (e.g., curved rail) as the robotic arm 101. The position of the robotic arm 101 and/or the arm 209 may be adjustable along the length of the support element 215. In other embodiments, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. In further embodiments, the robotic arm 101 and/or the optical sensing device 111 may be mounted to a separate mobile shuttle, as described in U.S. application Ser. No. 15/706,210, filed on Sep. 15, 2017, which is incorporated by reference herein. Although a single robotic arm 101 is shown in FIG. 1, it will be understood that two or more robotic arms 101 may be utilized. In addition, various embodiments of a computer-assisted surgical method or system may include image-guided or navigation-supported surgery without the use of a robotic arm 101.

The at least one robotic arm 101 may aid in the performance of a surgical procedure, such as a minimally-invasive spinal surgical procedure or various other types of orthopedic, neurological, cardiothoracic and general surgical procedures. In embodiments, the motion tracking system 105 may track the position of the robotic arm 101 (e.g., via marker device 202 on end effector 102 as shown in FIG. 1) within the patient coordinate system. A control loop may continuously read the tracking data and the current parameters (e.g., joint parameters) of the robotic arm 101 and may send instructions to a robotic controller to cause the robotic arm 101 to move to a desired position and orientation within the patient coordinate system.

In embodiments, a surgeon may use an image-guided surgery system as a planning tool for a surgical procedure, such as by setting trajectories within the patient for inserting surgical tools, as well as by selecting one or more target locations for a surgical intervention within the patient's body. The trajectories and/or target locations set by the surgeon may be saved (e.g., in a memory of a computer device, such as computer device 113 shown in FIG. 1) for later use during surgery. In embodiments, the surgeon may be able to select stored trajectories and/or target locations using an image guided surgery system, and the robotic arm 101 may be controlled to perform a particular movement based on the selected trajectory and/or target location. For example, the robotic arm 101 may be moved to position the end effector 102 of the robotic arm 101 into alignment with the pre-defined trajectory and/or over the pre-determined target location. The end effector 102 may include a hollow tube or cannula which may be used to guide an instrument 104 into the patient's body along the pre-defined trajectory and/or to the pre-defined target location. Alternately, the end effector 102 itself may be or may include an instrument that may be inserted into the patient's body and guided along the pre-defined trajectory and/or to the pre-defined target location.

Various embodiments include methods and systems for setting trajectories in a patient for image guided surgery. FIG. 2A schematically illustrates a system 201 for performing image guided surgery that includes a tracked instrument 204 used to define and set a trajectory within the body of a patient 200. In embodiments, the instrument 204 may be a handheld instrument that may be gripped and easily manipulated by a user (e.g., a surgeon), and may include an elongated portion 206 (e.g., a shaft) defining a longitudinal axis, a. The elongated portion 206 may narrow to a point at a tip end 208 of the instrument 204.

The instrument 204 may further include at least one marker device 120 to enable the instrument 204 to be tracked using a motion tracking system 105, as described above. In this embodiment, the at least one marker device 120 includes an array of reflective spheres that are rigidly fixed to the instrument 204, although other types of active or passive markers may be utilized. The marker device 120 may be in a known, fixed geometric relationship with the instrument 204 such that by tracking the marker device 120 the motion tracking system 105 may determine the position and/or orientation of the instrument 204. In embodiments, the instrument 204 and marker device 120 may be pre-calibrated so that the geometric relationship of one or more features of the instrument 204 (e.g., the tip of the instrument) may be precisely known in relation to the marker device 120.

The instrument 204 may further include a user-interface component, such as at least one button 210, to enable a user to enter user-commands. In the embodiment of FIG. 1, the instrument 204 may include circuitry 212 configured to detect an input event (e.g., a button push) at the user-interface component and transmit a user-command signal to a separate entity, such as computer 113. In some embodiments, the circuitry 212 may include wireless transceiver circuitry configured to transmit user-command signals wirelessly using a suitable wireless communication protocol or standard (e.g., an IEEE 802.15x (BLUETOOTH®) connection or IEEE 802.11 (WiFi) connection). The instrument 204 may include a power supply 214 (e.g., battery source) to provide power to electronic components of the instrument 204. The computer 113 may also include transceiver circuitry 216 to receive user-command signals transmitted from the instrument 204. Alternately, the instrument 204 may be connected to the computer 113 via a wired link that may be used to exchange data signals and/or provide power to the instrument 204.

In some embodiments, the instrument 204 may be a handheld pointer or stylus device that may be manipulated by the surgeon to point to or touch various locations on the skin surface of the patient 200. Alternately, the instrument 204 may be an invasive surgical instrument (e.g., dilator, cannula, needle, scalpel, drill, screwdriver, etc.) that may be inserted into the body of the patient. In some embodiments, the instrument 204 may comprise a portion of an end effector 102 of a robotic arm 101 that may be manipulated by a surgeon, such as by operating the robotic arm 101 in a hand-guided mode.

In embodiments, the instrument 204 may be a sterile component that may be usable within the surgical field with or without surgical draping and may be a single-use disposable component. In other embodiments, the instrument 204 may be re-sterilizable (e.g., autoclavable), and may be a reusable component.

As shown in FIG. 2A, the instrument 204 may be located within the range (e.g., field-of-view) of a sensing apparatus 111 of a motion tracking system 105. In the case of an optically-based motion tracking system 105, the sensing apparatus 111 may comprise an optical sensing device 111, which may be an array of cameras 207. The sensing apparatus 111 may detect electromagnetic radiation (e.g., IR optical radiation) that is transmitted (e.g., reflected or emitted from) the marker device 120. The detected radiation from the marker device 120 may be used by the motion tracking system 105 to determine the current position and/or orientation (i.e., pose) of the instrument 204 using, for example, triangulation techniques. The motion tracking system 105 may also track the current position and orientation of the patient 200 via a separate marker device 115 which may be rigidly attached to the patient 200 (e.g., clamped or otherwise attached to a bony portion of the patient's anatomy). The motion tracking system 105 may thereby continuously track the position and/or orientation of the instrument 204 relative to the patient (i.e., within a common, patient-centric coordinate system).

Patient images 218, which may have previously-been obtained by an imaging device 103, may be registered to the common patient-centric coordinate system using an image registration technique, as described above. One or more patient images 218 may be shown on a display screen of a display device 121, as shown in FIG. 2A. The patient images 218 may be displayed in conjunction with one or more graphical elements indicating the current position/orientation of the instrument 204 within the patient-centric coordinate system. For example, as shown in FIG. 2A, a dashed line 220 superimposed over the patient image 218 may indicate the trajectory defined by an imaginary ray 222 extending along axis a from the tip end 208 of the instrument 204 and into the patient 200. As the instrument 204 is moved relative to the patient 200, the location of the graphical element(s) 220 on the display screen may be updated to reflect the current pose of the instrument 204 relative to the patient.

In some embodiments, a detected movement of the instrument 204 may cause one or more different patient images 218 to be displayed on the display device 121. For example, moving the instrument 204 along the length of the patient may cause different axial slices of a 3D patient image dataset (e.g., CT reconstruction) to be displayed corresponding to the current location of the instrument 204. Similarly, a detected motion of the instrument 204 may cause a corresponding change in sagittal and/or coronal slices or in a three-dimensional volume rendering displayed by the display device 121. In embodiments, the surgeon may move through the various slices/views of the patient image volume shown on the display device 121 by moving the instrument 204 to various poses with respect to the patient 200. This may enable the surgeon to visualize multiple trajectories or paths extending from the patient's skin surface through the patient to particular anatomic features of interest. Each of the slices/views shown on the display device 121 may include one or more graphical elements 220 illustrating the trajectory into the patient 200 defined by the instrument 204. Alternately, the slices/views shown on the display device 121 may remain static and the display device 121 may show graphical depictions of the tracked instrument(s) 204 overlaying the patient images.

In embodiments, the user (e.g., surgeon) may set a particular trajectory defined by the instrument 204 by registering an input event using the user-interface component of the instrument 204. For example, the user may manipulate the instrument pose until the instrument 204 defines a desired trajectory into the patient, as may be indicated by graphical element(s) 220 overlaying the patient image(s) 218 displayed on the display device 121. The user may then actuate the user-interface component on the instrument 204, such as by pressing a button 210 as shown in FIG. 2A. The circuitry 212 within the instrument 204 may detect the input event (e.g., button push) made by the user and in response may transmit a user-command signal to the computer 113. The user-command signal may be a wireless (e.g., BLUETOOTH® or WiFi) signal.

The computer 113 may receive the user-command signal from the instrument 204 and in response may save the current trajectory defined by the instrument 204 in a memory. The trajectory may be saved in association with a unique identifier (e.g., file name). The computer 113 may also update the display screen of the display device 121 to indicate that a particular trajectory has been set by the user. For example, after a trajectory is set, graphical indicator (e.g., the dashed line 220 in FIG. 2A) indicating the current trajectory defined by the instrument 204 may be changed to a different color, brightness and/or line density (e.g., may change from a dashed to a solid line) and/or may include a label or other indicator to indicate that the trajectory has been set and saved for an image-guided surgical procedure. The visual indicator(s) of a particular set trajectory may continue to be depicted on the display device 121 even as the instrument 204 is moved to other positions and/or orientations with respect to the patient 200.

In some embodiments, the computer 113 may temporarily store the current trajectory defined by the instrument 204 in response to receiving a user-command signal from the instrument 204 (e.g., a button push) and may require a further input from the user before saving the trajectory as a set trajectory in a surgical navigation system. For example, in response to a detected button push event, the computer 113 may cause a prompt (e.g., an audio prompt from a speaker and/or a visual prompt on the display device 121) to be provided the user to confirm or reject the temporarily-stored trajectory. The user may respond to the prompt, such as via a voice command and/or an input event on a user interface, to either confirm or reject the temporarily-stored trajectory. A graphical indicator on the display device 121, such as a color code, may indicate that a trajectory is a temporarily-stored trajectory that is awaiting confirmation from the user.

The user (e.g., surgeon) may set multiple trajectories in the manner as described above, and each trajectory may be saved in association with a unique identifier (file name). Each of the trajectories may be defined and saved within a common patient-centric coordinate system, which as noted above, may be fixed with respect to a marker device 115 that is rigidly secured to a nearby anatomic feature (e.g., a bony structure). Thus, the surgeon may later return to the same pre-set trajectories with respect to the patient's anatomy, even if the patient 200 has been subsequently moved from an initial position.

Further embodiments may also include methods and systems for setting one or more target locations in a patient for image guided surgery. In some embodiments, a target location may be defined as a point at a particular depth along a trajectory extending into the body of a patient 200. FIGS. 2B-2C schematically illustrates a system 201 for using a tracked instrument 204 to define and set a target location within the body of a patient 200. The system 201 and tracked instrument 204 may be substantially identical to the system 201 and instrument 204 described above with reference to FIG. 2A. As shown in FIG. 2B, the instrument 204 may be used to define a trajectory into the patient, where the trajectory may extend along an imaginary ray 222 projected forward from the tip end 208 of the instrument 204. The trajectory defined by the instrument 204 may be represented by one or more graphical elements (e.g., dashed line 220) displayed over a patient image 218 on the display device 121.

In the embodiment of FIGS. 2B-2C, the user may define a target location based on a motion of the instrument 204 that is tracked by the motion tracking system 105. In embodiments, the motion of the instrument 204 may be a displacement of the instrument away from the patient 200.

The displacement of the instrument 204 away from the patient 200 may be in a direction that is substantially parallel to a pre-defined trajectory through the patient 200. For example, the user may use the instrument 204 to set a trajectory as described above with reference to FIG. 2A. After setting the trajectory, the user may then move the instrument 204 away from the patient 200 as shown in FIG. 2B. The motion tracking system 105 may track the displacement of the instrument 204 away from the patient, indicated by arrow d in FIG. 2B. The displacement may be an absolute displacement from the patient 200 (i.e., distance from the skin surface of the patient 200) or a relative displacement from an initial position of the instrument 204, where the initial position may or may not coincide with the skin surface of the patient 200. The displacement may be in a direction that is substantially parallel to the pre-defined trajectory through the patient. As used herein, "substantially parallel" means a direction that is within 45° from true parallel.

The display device 121 may display a patient image 218 in conjunction with at least one graphical element 224 indicating a depth, d', within the patient's body, where the depth, d' may be based on the displacement of the instrument 204 away from the patient 200 that is tracked by the motion tracking system 105. The depth d' may correspond to a distance from the skin surface of the patient 200 and along the pre-determined trajectory into the patient 200. The magnitude of the depth, d', may be proportional to the magnitude of the displacement, d, of the instrument 204, and in some embodiments may be equal to the magnitude of the displacement. In some embodiments, the magnitude of the depth, d', may vary non-linearly with the magnitude of the displacement, d, of the instrument 204. For example, the magnitude of the depth d' may increase at a relatively faster rate as the instrument 204 is initially moved away from the patient 200, and as the instrument 204 continues to move away from the patient 200 the rate at which the depth d' increases may slow down to enable more precise control for selection of a target location. In the embodiment of FIG. 2B, the depth d' is represented on the display device 121 as a line segment 224 overlaying the graphical representation of the trajectory (i.e., dashed line 220), where the length of the line segment 224 may vary as a function of the displacement of the instrument 204. As the instrument 204 is moved further away from the patient 200, the length of the line segment 224 shown on the display device 121 may increase, as shown in FIG. 2C. The depth d' may be represented on the display device 121 in any perceptible manner, such as by a point or other icon that moves over the patient image 218 based on the measured displacement of the instrument 204.

The user may adjust the displacement of the instrument 204 until the indicator of the depth, d', on the patient image(s) 218 shown on the display device 121 corresponds to a desired target location within the patient's body. As shown in FIG. 2C, for example, the indicator of the depth, d' (i.e., line segment 224) is shown extending to an anatomic structure depicted in the patient image 218. The user may then actuate the user-interface component on the instrument 204, such as by pressing a button 210. The button 210 may be the same or a different button as is used for setting a trajectory as described above. The circuitry 212 within the instrument 204 may detect the input event (e.g., button push) made by the user and in response may transmit a user-command signal to the computer 113. The user-command signal may be a wireless (e.g., BLUETOOTH® or WiFi) signal.

The computer 113 may receive the user-command signal from the instrument 204 and in response may save a target location, TL, in a memory. The target location, TL, may correspond to a point within the patient 200 along the pre-determined trajectory and at the desired depth, d'. The target location, TL, may be saved in association with a unique identifier (e.g., file name). The computer 113 may also update the display screen of the display device 121 to indicate that a particular target location has been set by the user. For example, after a target location is set, a graphical indicator (e.g., point P in FIG. 2C) may indicate a set target location superimposed on the patient image(s) 218.

In some embodiments, the computer 113 may temporarily store the current point defined by the instrument 104 in response to receiving the user-command signal from the instrument 204 and may require a further input from the user before saving the point as a target location, TL. For example, in response to a detected button push event, the computer 113 may cause a prompt (e.g., an audio prompt from a speaker and/or a visual prompt on the display device 121) to be provided the user to confirm or reject the temporarily-stored point. The user may respond to the prompt, such as via a voice command and/or an input event on a user interface, to either confirm or reject the temporarily-stored point. A graphical indicator on the display device 121, such as a color code, may indicate that a point is a temporarily-stored point that is awaiting confirmation from the user as a defined target location, TL.

The user (e.g., surgeon) may set multiple target locations in the manner as described above, and each target location may be saved in association with a unique identifier (file name). Each of the target locations may be defined and saved within a common patient-centric coordinate system, which as noted above, may be fixed with respect to a marker device 115 that is rigidly secured to a nearby anatomic feature (e.g., a bony structure). Thus, the surgeon may later return to the same pre-set target locations with respect to the patient's anatomy, even if the patient 200 has been subsequently moved from an initial position.

In addition to setting trajectories and/or target locations, in some embodiments, the instrument 204 may be used more generally as a user-interface device in an image guided surgery system. In embodiments, the instrument 204 may enable users to interact with and manipulate items on a display screen via gesture recognition and/or pointing. For example, the user may hold the instrument 204 within the field-of-view of the optical sensing device 111 to enable motion tracking of the instrument 204. The user may move or otherwise manipulate the instrument 204 to manipulate or interact with objects on the display device 121, such as by moving a cursor/icon, scrolling, panning, changing the image dataset shown on the screen, displaying different slice(s) and/or different 3D rendering(s) within an image dataset, zooming in or out of an image, displaying different menu options, returning to a home screen, etc. In one non-limiting example, moving a tracked instrument 204 towards or away from the optical sensing device 111 may cause the display device 121 to scroll through different slices (e.g., axial, sagittal and/or coronal slices) of a patient image dataset. A rotation of the instrument 204 may cause the display device 121 to make a corresponding rotation of a three-dimensional rendering of the image data. In some embodiments, the user may enter selections via an interface component (e.g., button 210) on the instrument 204, or via another means, such as by voice recognition or command gestures that may be recognized by the motion tracking system.

Figure 3:
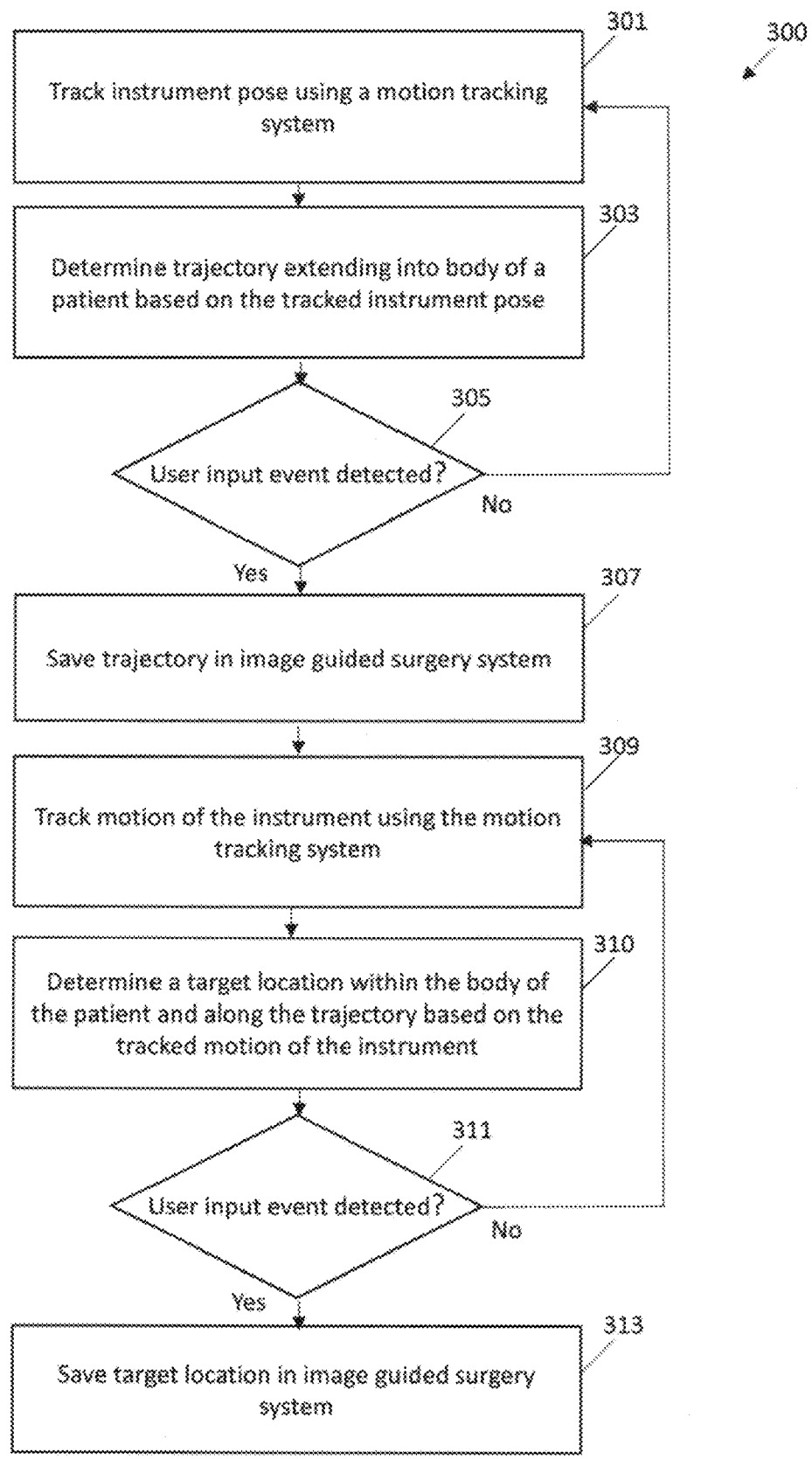
FIG. 3 is a process flow diagram illustrating a method for setting and saving trajectories and target locations within a patient for image-guided surgery.

FIG. 3 is a process flow diagram illustrating an embodiment method 300 for setting trajectories and target locations for image-guided surgery. The method 300 may be implemented using a system 201 as described above with reference to FIGS. 2A-2C. However, it will be appreciated that other image-guided surgery systems may be used to practice the method 300 in various embodiments.

In block 301 of method 300, an instrument pose may be tracked using a motion tracking system. The instrument may be a pointer or stylus device having a marker device attached thereto that may enable the instrument to be tracked by the motion tracking system. Alternately, the instrument may be an invasive surgical instrument and/or a portion of an end effector of a robotic arm. The motion tracking system may track the pose of the instrument by determining the position and/or orientation of the instrument relative to a patient.

In block 303 of method 300, a trajectory extending into the body of a patient may be determined based on the tracked instrument pose. In embodiments, the position and/or orientation of the instrument may define a unique trajectory into the body of the patient. For example, as discussed above with reference to FIG. 2A, the unique trajectory may be defined by a ray projected forward into the patient from a tip end of the instrument and extending parallel to a major axis of the instrument. The location of the trajectory in three-dimensional space may be determined by the motion tracking system based on the detected position of the marker device and the known geometry of the instrument. A graphical indicator of the trajectory within the body of the patient may be displayed on a display device.

In determination block 305, a determination may be made whether a user input event is detected. In response to a determination that no user input event is detected (i.e., determination block 305="No"), then the instrument pose may continue to be tracked using a motion tracking system in block 301 and the trajectory based on the tracked instrument pose may be determined in block 303.

In response to a determination that a user input event is detected (i.e., determination block 305="Yes"), the trajectory may be saved in an image guided surgery system in block 307. The user input event, may include, for example, a voice command, a touch event on a touchscreen interface (e.g., on a display device 121), and/or an input on a user interface device (e.g., a keyboard entry, a mouse click, a button push, etc.). In some embodiments, the user input event may be made via the tracked instrument, which may include a user interface component (e.g., a button) and circuitry (e.g., a BLUETOOTH® and/or WiFi transceiver) for sending user command signals to a separate computing device.

In block 309, a motion of the instrument may be tracked by the motion tracking system. The motion may be a displacement of the instrument away from the patient. The tracking of the instrument may include determining a distance by which the instrument is displaced. In block 310, a target location within the body of the patient and along the trajectory may be determined based on the tracked motion of the instrument. In embodiments, the target location may correspond to a depth within the patient and along the trajectory. A graphical indicator of the target location within the body of the patient may be displayed on a display device.

In determination block 311, a determination may be made whether a user input event is detected. In response to a determination that no user input event is detected (i.e., determination block 311="No"), the motion of the instrument may continue to be tracked by the motion tracking system in block 309 and the target location based on the tracked movement of the instrument may be determined in block 310.

In response to a determination that a user input event is detected (i.e., determination block 311="Yes"), the target location may be saved in an image guided surgery system in block 313. The user input event, may include, for example, a voice command, a touch event on a touchscreen interface (e.g., on a display device 121), and/or an input on a user interface device (e.g., a keyboard entry, a mouse click, a button push, etc.). In some embodiments, the user input event may be made via the tracked instrument, which may include a user interface component (e.g., a button) and circuitry (e.g., a BLUETOOTH® and/or WiFi transceiver) for sending user command signals to a separate computing device.

Figure 4:
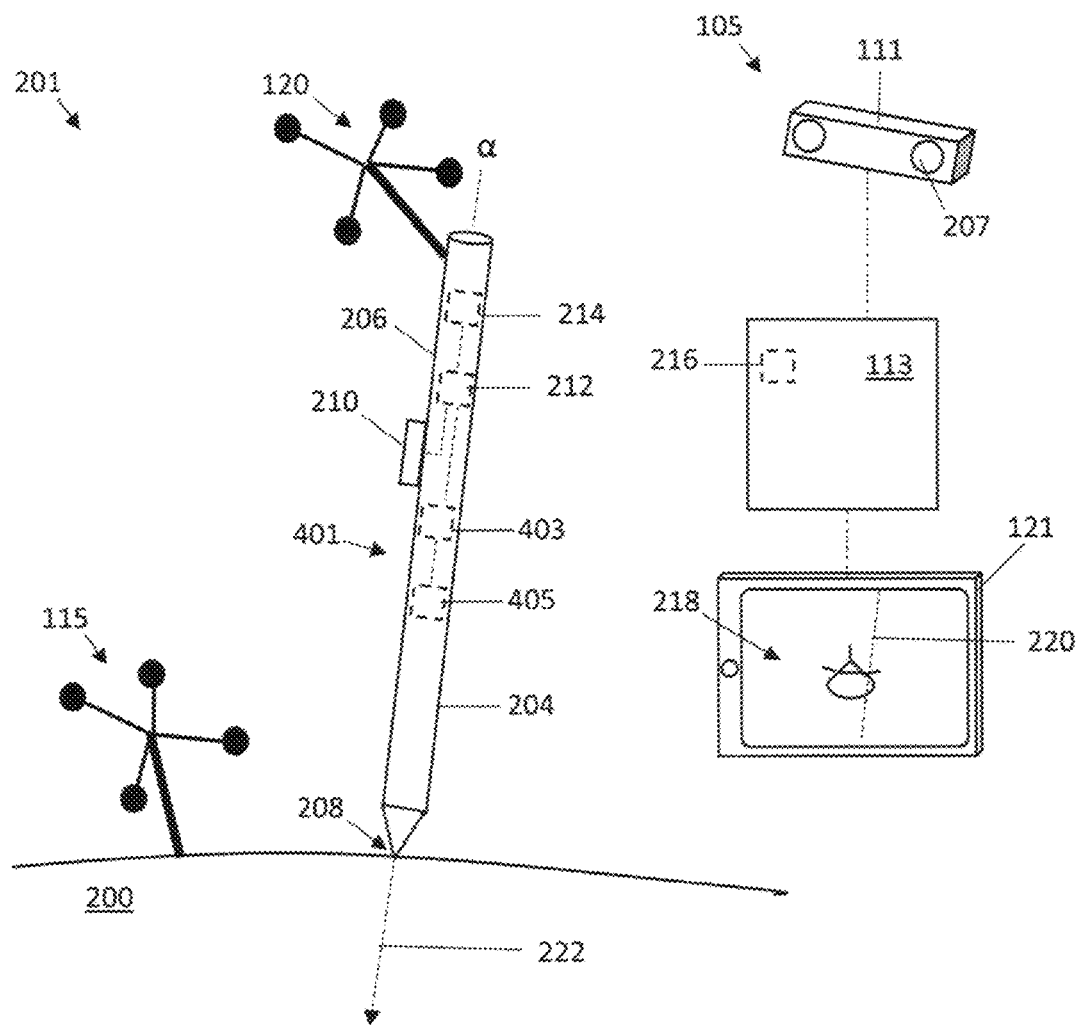
FIG. 4 illustrates a tracked instrument having an inertial measurement unit.

FIG. 4 illustrates a further embodiment of a system 201 for performing image guided surgery that includes a tracked instrument 204 having an inertial measurement unit 401. The inertial measurement unit 401 may be in addition to a marker device 120 for an optically-based motion tracking system 105, as described above. In embodiments, the inertial measurement unit 401 may enable redundant motion tracking of the instrument 204. In particular, the position and/or orientation of the instrument 204 may continue to be tracked when there is a loss of tracking by the optically-based motion tracking system 105, such as when the line of sight between marker device 120 and optical sensing device 111 is temporarily obscured.

The inertial measurement unit 401 may enable inertial navigation of the tracked instrument 204. In embodiments, the inertial measurement unit 401 may include a three-axis accelerometer 403 and a three-axis gyroscope 405. The accelerometer 403 and gyroscope 405 may be fabricated utilizing MEMS technology. The accelerometer 403 and gyroscope 405 may be separate components (e.g., chips) located in the instrument 204 or may be integrated on a single device (e.g., integrated circuit). The instrument 204 may also include circuitry 212 coupled to the accelerometer 403 and gyroscope 405 that may be configured to read output signals from these components 403, 405. The accelerometer 403 may output signals measuring the linear acceleration of the instrument 204, preferably in three-dimensional space. The gyroscope 405 may output signals measuring the angular velocity of the instrument 204, preferably also in three-dimensional space. The signals from the accelerometer 403 and gyroscope 405 may be processed using a suitable processor, such as a computer 113, to determine the position and orientation of the instrument 204 with respect to an initial inertial reference frame via a dead reckoning technique. In particular, integrating the angular velocity measurements from the gyroscope 304 may enable the current orientation of the instrument 204 to be determined with respect to a known starting orientation. Integrating the linear acceleration measurements from the accelerometer 403 may enable the current velocity of the instrument 204 to be determined with respect to a known starting velocity. A further integration may enable the current position of the instrument 204 to be determined with respect to a known starting position.

In embodiments, measurement data from the inertial measurement unit 401 may transmitted from the tracked instrument 204 to a separate computing device (e.g., computer 113) via a wired or wireless link. In embodiments, the data may be transmitted wirelessly using a suitable wireless communication protocol or standard (e.g., an IEEE 802.15x (BLUETOOTH®) or IEEE 802.11 (WiFi) connection), as described above. The computer 113 may perform the inertial navigation calculations to determine the position and orientation of the instrument 204 in three-dimensional space, and preferably within the common, patient-centric coordinate system. The inertial navigation calculations may be initialized with a known initial position, orientation and/or velocity of the instrument 204, which may be or may be derived from the most recent tracking data from the motion tracking system 105.

Alternately, at least a portion of the inertial navigation calculations may be performed on the instrument 204, such as on a processor (e.g., microprocessor) located in the instrument 204. The inertial navigation may be initialized using motion tracking data from an external source (e.g., computer 113 or motion tracking system 105), which may be received by the instrument 204 over a wired or wireless link.

In embodiments, the inertial navigation of the instrument 204 may be performed in parallel with motion tracking using an optically-based motion tracking system 105. In embodiments, the optically-based motion tracking data and the inertial navigation data may be fused in the image guided surgery system, such as using a Kalman filter.

Alternately, inertial navigation may only be performed on an intermittent basis, such as in response to a triggering signal that may be transmitted from the computer 113 to the instrument 204 via a wired or wireless (e.g., BLUETOOTH® or WiFi) communication link. In embodiments, the inertial navigation may be triggered in response to a tracking failure of the optically-based motion tracking system 105, which may result from a temporary blocking of a camera 207 or the marker device 120. By tracking the instrument 204 using inertial navigation when accurate optical tracking data is not available, this may enable the instrument 204 to be continuously tracked. When the optical tracking system 105 resumes tracking of the instrument 204, a signal may be transmitted to the instrument 204 to discontinue the inertial navigation.

When tracking the instrument 204 by inertial navigation, the accuracy of the tracking may be acceptable over a particular time frame, which may be known or determined empirically. Inertial navigation is subject to drift, which may accumulate over time to produce tracking accuracy errors that may increase as a function of time. Thus, after a pre-determined time period, the inertial navigation data may not be sufficiently accurate to support continued tracking of the instrument 204 absent a position state update using data from another source (e.g., the optical motion tracking system 105). In embodiments, the image guided surgery system may be configured to determine whether the inertial navigation data satisfies one or more navigation accuracy criteria for tracking the position and/or orientation of the instrument 204. In embodiments, the navigation accuracy criteria may include a time limit for tracking using only inertial navigation. The image guided surgery system may notify the user (e.g., via an audible and/or visual alert) in response to determining that the navigation accuracy criteria is not satisfied. The notification to the user may be provided on the display screen of a display device 121. In embodiments, the image guided surgery system may discontinue navigation of the instrument 204 until new motion tracking data from the motion tracking system 105 is acquired.

In some embodiments, multiple inertial measurement units 401, each unit including a three-axis accelerometer 403 and a three-axis gyroscope 405, may be located on or within the tracked instrument 204. Inertial navigation of the instrument 204 may be performed based on data measured by each unit 401, where the position and orientation of the instrument 204 may be based on an average of the results from each unit. This may enable accurate inertial navigation over a longer time period than when using a single inertial measurement unit. The image guided surgery system may notify the user (e.g., via an audible and/or visual alert) in response to determining that the inertial navigation is no longer considered accurate, which may be after pre-determined time period and/or when a variance in the calculated position and/or orientation of the instrument from a plurality of inertial measurement units exceeds a threshold value.

Figure 5:
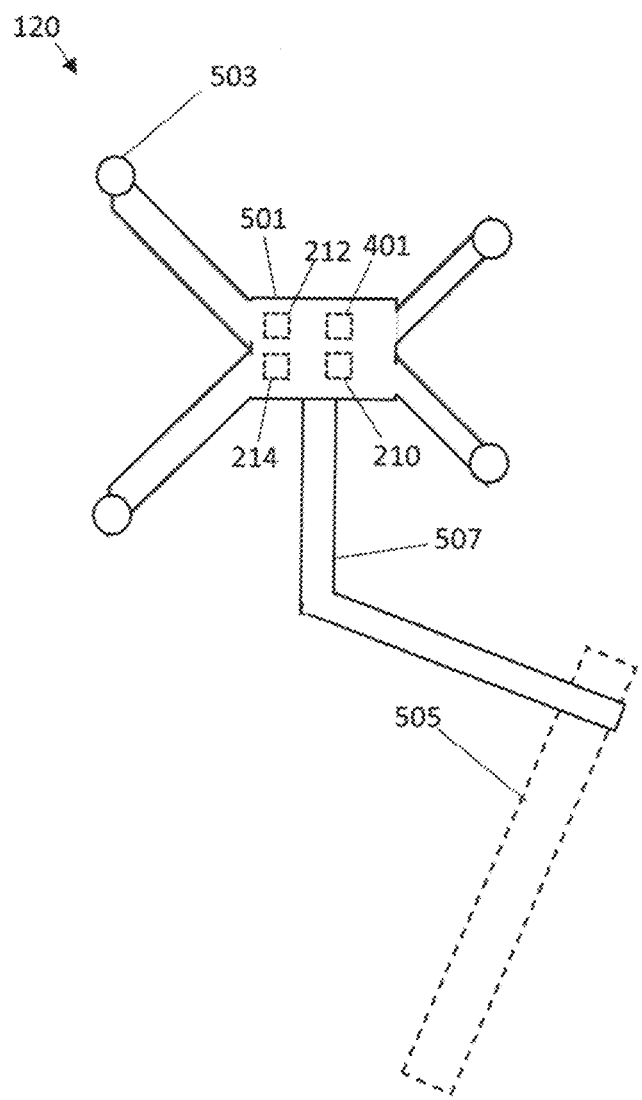
FIG. 5 illustrates an array of optical tracking markers having a wireless transceiver and inertial measurement unit located on the array of optical tracking markers.

FIG. 5 illustrates a marker array 120 including a plurality of optical markers 503 (e.g., reflective spheres) on a rigid-frame 501. The optical markers 503 may be arranged in a unique pattern on the frame 501 to enable the marker array 120 to be identified and tracked by the motion tracking system 105. The frame 501 may also include a power supply 214 (e.g., battery), electronic circuitry 212 including wireless transceiver circuitry, and an inertial measurement unit 401 that may include a three-axis accelerometer and a three-axis gyroscope, as described above. The marker array 120 may be attached to a surgical instrument 505 via a rigid elongate attachment member 507, which may be a bent or curved rod. The surgical instrument 505 may be a handheld pointer or stylus device as described above, or may be an invasive surgical tool that may be inserted into the body of a patient during a surgical procedure. Examples of such tools include, without limitation, a needle, a cannula, an awl, a drill, a screw driver, a tool for gripping or cutting, an electrode, a radiation source, and an endoscope. The marker array 120 may be integrally formed on the instrument 505 or may be attached (e.g., retrofit) onto an existing instrument 505 via a suitable attachment mechanism. The instrument 505 may be registered in association with the marker array 120 in an image guided surgery system so that the position and/or orientation of the instrument 505 may be tracked in 3D space and optionally illustrated on a display 121. In some embodiments, the frame 501 of the marker array 120 may also include a user-interface component, such as at least one button 210, to enable a user to enter user-commands. The commands may be transmitted wirelessly to an external device (e.g., computer 113 shown in FIGS. 2A-2C and 4). In embodiments, the instrument 505 may be used to set target trajectories and/or locations as described above and may be used to perform other user-interface functions in an image guided surgery system. The inertial measurement unit 401 may perform inertial navigation of the instrument 505 as discussed above with reference to FIG. 4. This may enable the instrument 505 to be tracked using optically-based motion tracking as well as inertial navigation, such as when optical tracking data is not available.

In some embodiments, the marker array may be a patient reference array 115, as described above. For example, rather than attaching to a surgical instrument 505, the attachment member 507 may include a bone clamp or similar fastening mechanism that enables the reference array to be rigidly attached to a portion of the patient's anatomy (e.g., a spinous process or iliac crest of the hip). This may enable the patient to be tracked using optically-based motion tracking as well as inertial navigation, such as when the line-of-sight to a camera array is blocked or other situations where optical tracking data is not available. In further embodiments, a marker array 120 such as illustrated in FIG. 5 may be attached to a portion of a robotic arm 101, such as an end effector 102, as shown in FIG. 1, to enable the arm 101 to be tracked in the patient coordinate system using optical motion tracking, inertial navigation, or both.

In further embodiments, a plurality of optical markers 503 (e.g., reflective spheres) may be attached to a portion of the robotic arm 101, such as on a rigid-frame 501 as shown in FIG. 5, and an inertial measurement unit 401 as described above may be mounted separately on or within the robotic arm 101. The inertial measurement unit 401 may be a high-performance (i.e., low drift) IMU that may be located at or proximate to the distal end of the robotic arm 101 (e.g., beyond the distal-most joint of the robotic arm 101). Power and/or data connections for the inertial measurement unit 401 may be provided through the robotic arm 101. Alternately or in addition, the inertial measurement unit 401 may be coupled to wireless transceiver circuitry to enable wireless communication with an external device, such as computer 113. The position and/or orientation of the end effector 102 may be tracked in the patient coordinate system using optical motion tracking, inertial navigation, or both. In embodiments, the inertial measurement unit 401 may enable inertial-based tracking of the end effector 102 with minimal lag time. The inertial tracking may be initialized using the optical tracking data from the motion tracking system 105, and may obtain a position state update using optical tracking data at a high rate (e.g., >60 Hz, such as 100 Hz or more, including 250 Hz) to minimize inaccuracies from integration drift.

Figure 6:
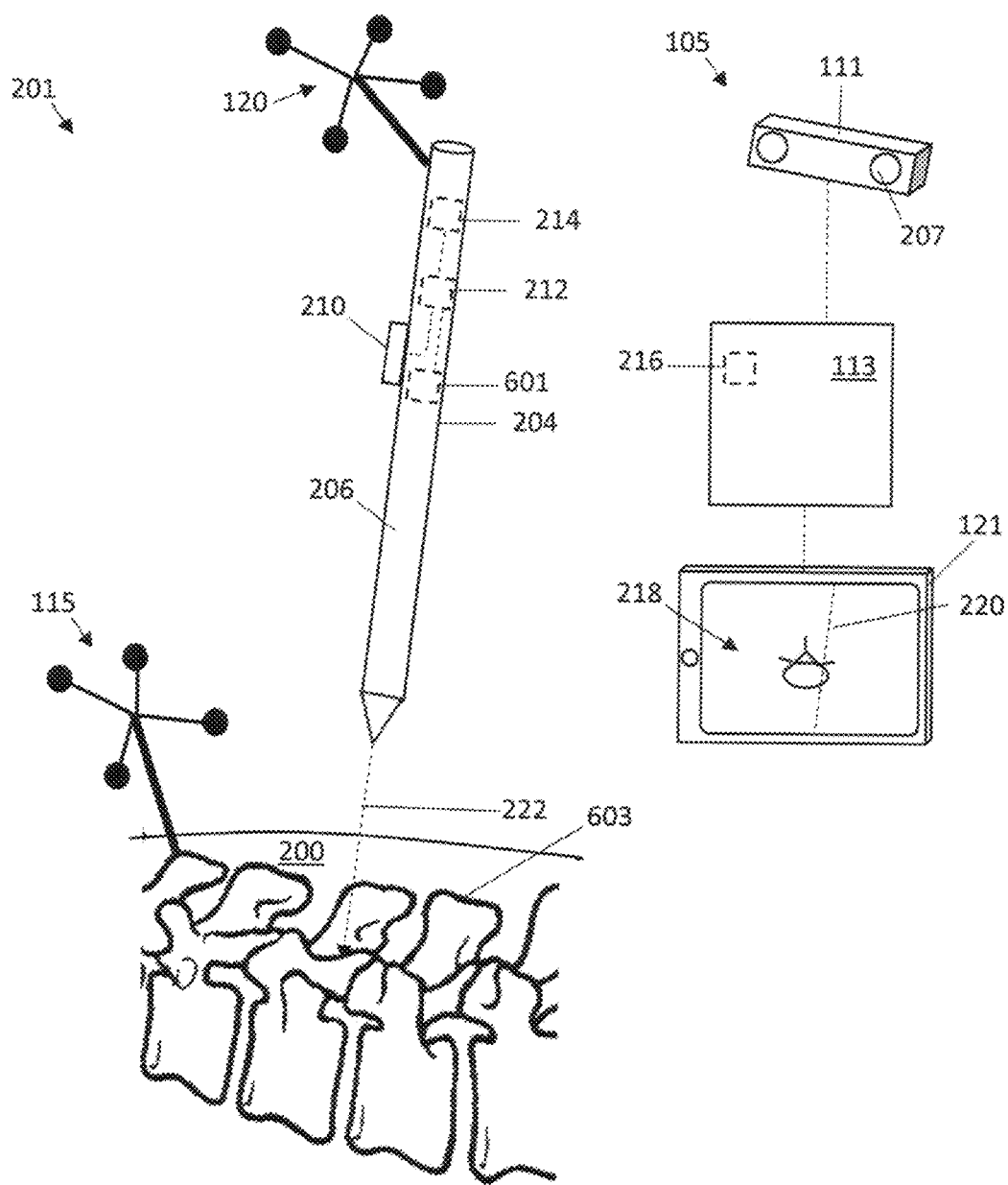
FIG. 6 schematically illustrates a tracked instrument that provides haptic feedback based on position over a patient's anatomy.

FIG. 6 illustrates a further embodiment of a system 201 for performing image guided surgery that includes a tracked instrument 204 having haptic feedback mechanism. The haptic feedback mechanism may be configured to provide haptic feedback (e.g., vibration) to a user based on the position and/or orientation of the instrument 204. The tracked instrument 204 may be similar to the instruments described above with reference to FIGS. 2A-2C, and may include a marker array 120 for a motion tracking system 105, a power supply 214 (e.g., battery), electronic circuitry 212 including wireless transceiver circuitry, and a haptic actuator 601, which may be a vibration motor (e.g., an eccentric rotating mass motor or linear resonant actuator). Alternately, the tracked instrument 204 may include a wired connection to provide power and signal/data communication. The tracked instrument 204 may also include a user-interface component, such as at least one button 210, to enable a user to enter user-commands. In some embodiments, the tracked instrument 204 may also include an inertial measurement unit for performing inertial navigation, as described above with reference to FIGS. 4 and 5.

Figure 7:
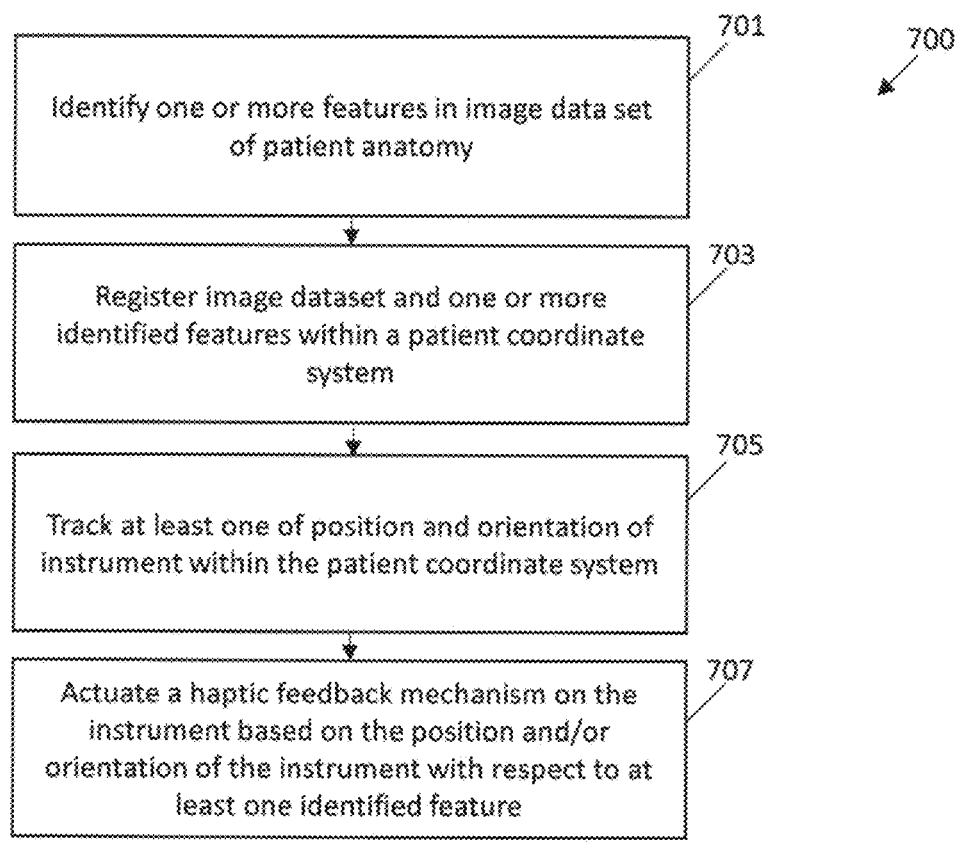
FIG. 7 is a process flow diagram illustrating a method for providing haptic feedback to a user based on the position of a tracked instrument relative to a patient.

FIG. 7 is a process flow diagram that illustrates a method 700 for provided haptic feedback to a user in an image guided surgery system based on the position of a tracked handheld instrument 204. The method 700 of FIG. 7 may be implemented using a system such as shown in FIG. 6. More particularly, various aspects of the method 700 may be implemented in software that may execute on one or more computing devices, such as computer 113 shown in FIG. 6. In block 701 of method 700, one or more anatomical features within the body of the patient may be identified in an image dataset of the patient's anatomy. The image dataset of the patient's anatomy may be obtained using an imaging device, such as the imaging device 103 shown in FIG. 1. The image dataset may be a three-dimensional dataset (e.g., a 3D CT tomographic reconstruction, a 3D MRI dataset, etc.) representing at least a portion of the patient's anatomy, including the internal anatomy and/or structure(s) that are to be operated on (i.e., a surgically-relevant portion of the patient's anatomy). The image dataset may be produced from multiple sources, such as a fused dataset of CT and MRI data. The image dataset may be stored electronically in a memory. The image dataset may be in any suitable format, such as in a file format that conforms to the Digital Imaging and Communications in Medicine (DICOM) standard.

In embodiments, the anatomical feature within the body of the patient may comprise a discrete anatomic structure and/or a tissue type. In embodiments, the anatomical feature may be a bone or skeletal feature, such as at least a portion of a spine of the patient. In other embodiments, the anatomical feature may be an internal organ or tissue portion, including an abnormal portion of tissue, such as a tumor. The anatomical feature may be identified by applying an image segmentation process to the image dataset. In the case of x-ray image data, for example, this may include calibrating radiodensity values (e.g., Hounsfield units) associated with different tissue types (e.g., bone vs. soft tissue) and applying a thresholding algorithm to the image dataset to identify one or more transitions between the different tissue types. A three-dimensional volume corresponding to the anatomical feature of interest may be identified within the image dataset.

In block 703, the image dataset including the identified anatomical feature may be registered within a patient coordinate system. In particular, the image dataset including the identified anatomical feature may be correlated with the patient position which may be determined using a motion tracking system 105 as described above.

In block 705, the position and/or orientation of a handheld instrument 204 may be tracked within the patient coordinate system. The instrument 204 may be tracked using a motion tracking system 105 as described above.

In block 707, a haptic feedback mechanism on the handheld instrument 204 may be actuated based on the position and/or orientation of the instrument with respect to the identified anatomical feature. In embodiments, the haptic feedback mechanism may be actuated when a trajectory defined by the instrument 204 intersects with the identified anatomic feature. For example, as shown in FIG. 6, the identified anatomic feature may be the bony portion of the spine 603 of the patient 200. The haptic feedback mechanism (e.g., haptic actuator 601) may be actuated when a ray 222 projected forward from a tip end of the instrument 204 and extending parallel to a major axis of the instrument 204 intersects with a bony portion of the spine 603 of the patient 200. This may provide an easily-perceptible tactile feedback to a user holding the instrument 204 that the instrument 204 is at a position and orientation that defines a trajectory into an anatomic feature of interest, such as a feature requiring surgical intervention and/or a feature to be avoided during a surgical intervention.

In embodiments, one or more characteristics of the haptic feedback may vary based on the relationship of the instrument 204 to one or more identified anatomic features of the patient 200. For example, a magnitude and/or a pattern of vibration of the instrument 204 may vary based on a profile of the tissue along the trajectory defined by the instrument 204. In one example, a first vibration magnitude/pattern may indicate bone, a second vibration magnitude/pattern may indicate fibrocartilaginous tissue (e.g., an intervertebral disc), a third vibration magnitude/pattern may indicate nervous tissue (e.g., the spinal cord and/or a peripheral nerve), a fourth vibration magnitude/pattern may indicate a circulatory structure (e.g., an artery or vein), etc. The system may be configured such that certain types of tissues or structures may produce a haptic feedback and others may not. In some embodiments, the haptic feedback may be provided based on an offset distance from the tip end of the instrument 204. For example, a pre-determined haptic feedback (e.g., vibration) signal may be provided when a point along the trajectory that is offset from the tip of the instrument 204 by a pre-determined distance is located in a first type of tissue or structure (e.g., bone). As the point is moved to a different type of tissue or structure within the patient, the haptic feedback may cease or change to a different type of haptic feedback signal. In some embodiments, the haptic feedback signal may be a function of the amount of a particular tissue or anatomic structure that the trajectory defined by the instrument 204 passes through. For example, the magnitude of vibration produced by the haptic feedback mechanism may increase as a function of the thickness of a particular tissue type (e.g., bone) through which the trajectory passes.

The haptic feedback mechanism on the instrument 204 may be selectively actuated by sending control signal(s) to the instrument 204. In embodiments, the control signal(s) may be sent wirelessly, such as via a BLUETOOTH® or WiFi connection.

Alternately or in addition, the haptic feedback mechanism on the handheld instrument 204 may be actuated based on the position and/or orientation of the instrument with respect to a preset target position and/or target trajectory inside the patient. For example, the haptic feedback mechanism may be actuated when a trajectory defined by the instrument 204 intersects with a preset target position or is aligned with a preset target trajectory. The target position and/or target trajectory may be previously set as described above with reference to FIGS. 2A-3, for example. This may provide an easily-perceptible tactile feedback to a user holding the instrument 204 that the instrument 204 is located over the anatomic feature of interest. This may be useful, for example, when the instrument 204 is an invasive instrument that is advanced into the patient's body. In some embodiments, a first type of haptic feedback signal (or no haptic feedback signal) may be actuated when the instrument 204 is properly aligned with the target position or along the target trajectory and a second type of haptic feedback signal, different from the first type of haptic feedback signal, may be actuated when the instrument 204 is misaligned with the target position or trajectory by a pre-determined threshold amount.

In one non-limiting embodiment, no haptic feedback signal may be generated when the instrument 204 is properly aligned with the target position or target trajectory, and a haptic feedback signal may be generated when the instrument 204 becomes misaligned with the target position or target trajectory. A characteristic of the haptic feedback signal may change (e.g., a magnitude of vibration may increase) as a function of the distance by which the instrument 204 is misaligned. Alternatively, a haptic feedback signal may only be generated when the instrument 204 is properly aligned with the target position or target trajectory.

Figure 8:
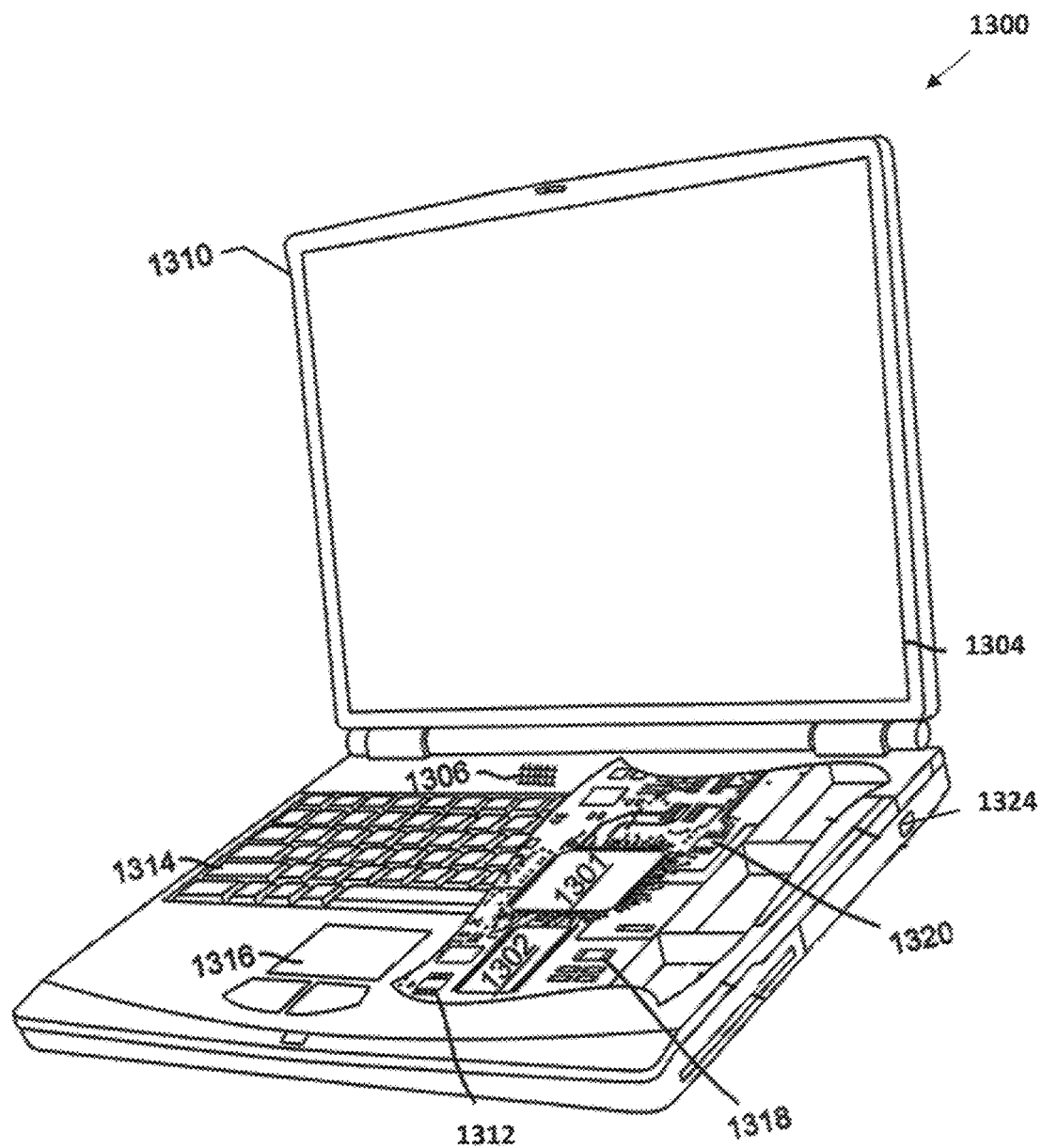
FIG. 8 schematically illustrate a computing device which may be used for performing various embodiments.

FIG. 8 is a system block diagram of a computing device 1300 useful for performing and implementing the various embodiments described above. The computing device 1300 may be used to perform image guided surgery, for example. While the computing device 1300 is illustrated as a laptop computer, a computing device providing the functional capabilities of the computer device 1300 may be implemented as a workstation computer, an embedded computer, a desktop computer, a server computer or a handheld computer (e.g., tablet, a smartphone, etc.). A typical computing device 1300 may include a processor 1301 coupled to an electronic display 1304, a speaker 1306 and a memory 1302, which may be a volatile memory as well as a nonvolatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. Additionally, the computing device 1300 may include network access ports 1324 coupled to the processor 1301 for establishing data connections with a network (e.g., LAN coupled to a service provider network, etc.). A laptop computer or desktop computer 1300 typically also includes a keyboard 1314 and a mouse pad 1316 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method for performing image guided surgery, comprising:
    tracking a surgical instrument using optically-based motion tracking;
    tracking the surgical instrument using inertial navigation when the optically-based motion tracking is not available, the inertial navigation including:
        measuring a linear acceleration and an angular velocity of the surgical instrument with an accelerometer and a gyroscope;
        transmitting a signal corresponding to the linear acceleration and the angular velocity to a computing device;
        receiving, at the computing device, the signal corresponding to the linear acceleration and the angular velocity; and
    notifying a user when an accuracy criteria for the inertial navigation is not satisfied.

2. The method of claim 1, wherein the accuracy criteria comprises a time period for tracking using inertial navigation without a position state update from an external source.

3. The method of claim 1, wherein tracking the surgical instrument using inertial navigation comprises receiving, at a computing device, measurement data from one or more inertial sensors located on the surgical instrument over a wireless communication link.

4. The method of claim 1, wherein the accuracy criteria further comprises a variance among tracking measurements obtained using multiple inertial sensors located on the surgical instrument.

5. The method of claim 1, wherein the linear acceleration of the surgical instrument is measured in a three-dimensional space.

6. The method of claim 1, wherein the angular velocity of the surgical instrument is measured in a three-dimensional space.

7. The method of claim 1, wherein tracking the surgical instrument using inertial navigation includes determining a position and an orientation of the surgical instrument with respect to an initial inertial reference frame via dead reckoning.

8. The method of claim 1, further comprising:
    initializing the surgical instrument based on a known initial position, a known initial orientation, a known velocity, or combinations thereof.

9. The method of claim 8, wherein initializing the surgical instrument is performed with optically-based motion tracking.

10. The method of claim 1, wherein notifying the user when accuracy criteria for the inertial navigation is not satisfied comprises activating an audible alert.

11. The method of claim 1, wherein notifying the user when accuracy criteria for the inertial navigation is not satisfied comprises activating a visual alert.

12. The method of claim 1, further comprising:
    discontinuing tracking of the surgical instrument using inertial navigation until new tracking data from the optically-based motion tracking is acquired.

13. A system for performing image-guided surgery, comprising:
    a surgical instrument including:
        at least one inertial sensor including an accelerometer and a gyroscope;
        an optical marker device; and
        a transmitter for transmitting data from the surgical instrument;
    a sensing device configured to receive electromagnetic signals that are reflected or emitted from the optical marker device;
    a receiver for receiving data transmitted from the surgical instrument; and
    a processing system, coupled to the sensing device and to the receiver, and including at least one processor configured with processor-executable instructions to perform operations comprising:
        tracking a surgical instrument using optically-based motion tracking;
        tracking the surgical instrument using inertial navigation when the optically-based motion tracking is not available, the inertial navigation including:
            measuring a linear acceleration and an angular velocity of the surgical instrument with the inertial sensor;
            transmitting a signal corresponding to the linear acceleration and the angular velocity to the receiver; and
        notifying a user when an accuracy criteria for the inertial navigation is not satisfied.

* * * * *